United States Patent [19]

Charmot et al.

[11] Patent Number: 5,395,903
[45] Date of Patent: Mar. 7, 1995

[54] CONJUGATED DIENE CHAIN-TRANSFER AGENTS FOR POLYMERIZATION OF OLEFINICALLY UNSATURATED (CO)MONOMERS

[75] Inventors: Dominique Charmot, Le Pre Saint Gervais; Nicole Oger, Nanterre, both of France; Heinz Viehe, Limal, Belgium

[73] Assignee: Rhone-Poulenc Chimie, Courbevoie, France

[21] Appl. No.: 149,789

[22] Filed: Nov. 10, 1993

[30] Foreign Application Priority Data

Nov. 10, 1992 [FR] France ............... 92 13520

[51] Int. Cl.$^6$ .............................. C08F 2/38
[52] U.S. Cl. ................. 526/220; 526/214; 526/222
[58] Field of Search ............. 526/220, 222, 214

[56] References Cited

U.S. PATENT DOCUMENTS

| 2,497,107 | 2/1950 | Weber | 526/214 |
| 5,194,539 | 3/1993 | Charmot et al. | 526/220 |

FOREIGN PATENT DOCUMENTS

| WO8804304 | 6/1988 | Austria . |
| 0130637 | 2/1985 | European Pat. Off. . |
| 0469954 | 6/1992 | European Pat. Off. . |

OTHER PUBLICATIONS

Polymerization Process–Schildknecht 1977 p. 18.
Chemical Abstracts, vol. 79, No. 11, 17 Sep. 1973, Columbus, Ohio, U.S. abstract No. 65709p, & Pogosyan et al-Arm. Khim. Zh. vol. 26, No. 4, 1973, pp. 339–340.
Chemical Abstracts, vol. 98, No. 19, 9 May 1983, Columbus, Ohio, US; abstract No. 159844y, & Graefing, R. et al, Recl. J. R. Neth. Chem. Soc. vol. 101, No. 10, 1982, pp. 346–351.
Tetrahedron Letters, vol. 30, No. 46, 1989, Oxford GB pp. 6405–6408, Tatsuo Hamada et al. Diels–Alder reaction of chiral dienes. Remarkable effect of dienophile polarity upon diastereo face selectivity.

*Primary Examiner*—Joseph L. Schofer
*Assistant Examiner*—N. Sarofim
*Attorney, Agent, or Firm*—Burns, Doane, Swecker & Mathis

[57] ABSTRACT

Odorless functional (co)polymers are prepared by polymerizing, for example via aqueous emulsion, bulk or organic solution polymerization, at least one olefinically unsaturated monomer, e.g., styrene, butadiene, a (meth)acrylate or a vinyl nitrile, in the presence of a molecular weight/crosslinking-regulating amount of a conjugated diene chain-transfer agent having the formula (1):

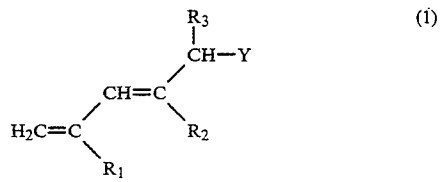

11 Claims, No Drawings

CONJUGATED DIENE CHAIN-TRANSFER AGENTS FOR POLYMERIZATION OF OLEFINICALLY UNSATURATED (CO)MONOMERS

BACKGROUND OF THE INVENTION

1. Field of the Invention

The present invention relates to the polymerization of ethylenically unsaturated (co)monomers in the presence of certain conjugated diene chain-transfer agents (or chain-limiting agents).

2. Description of the Prior Art

To restrict or limit molecular weight and/or the degree of crosslinking of the ultimate polymers, conventional polymerizations require use of a chain-transfer agent (or chain-limiting agent), which elicits its intended effect during the polymerization process. The transfer agents currently used industrially include aliphatic mercaptans and halogenated hydrocarbons. Advantages are associated with each of these two types of regulating agents. Although they have a very low residual mercaptan content, the polymers produced in the presence of a mercaptan typically possess an undesirable odor. If organohalogenated compounds are used, such as carbon tetrachloride, bromoform, or bromotrichloromethane (see, for example, U.S. Pat. No. 4,176,219), the residual amounts thereof are relatively high.

U.S. Pat. No. 3,726,832 describes the preparation of polymers of conjugated diolefins having a molecular weight of less than one million, at a high polymerization rate, and using cyclic ethers as the agent regulating the molecular weight.

WO-A-88/04,304 describes a chain-transfer agent selected from among compounds corresponding to the formulae:

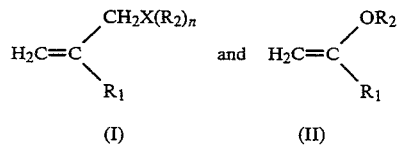

(I)          (II)

wherein $R_1$ is preferably a radical, such as an aromatic radical capable of activating the ethylenic double bond; $R_2$ is, in particular, an alkyl radical, and X is a heteroatom.

According to such '304 patent, the chain-transfer agents having the formulae (I) and (II) possess a chain-transfer constant of approximately 1, thereby enabling production of polymers having a narrow molecular weight distribution.

SUMMARY OF THE INVENTION

Accordingly, a major advantage of the present invention is the provision of an improved polymerization technique, providing good monomer conversion, to produce polymers or copolymers possessing little or no undesirable odor or residual halogenated compounds, without requiring a post-polymerization treatment or elimination of the residual transfer agent.

Another object of the present invention is the provision of novel transfer agents possessing a chain-transfer constant of approximately 1, which yield polymers having the desired chain length, and which comprise conjugated diene functional groups.

Briefly, the present invention features novel chain-transfer agents for the polymerization of olefinically unsaturated co(monomers), which avoid or conspicuously ameliorate the above disadvantages and drawbacks to date characterizing the state of this art, said novel chain-transfer agents comprising conjugated dienes having the general formula:

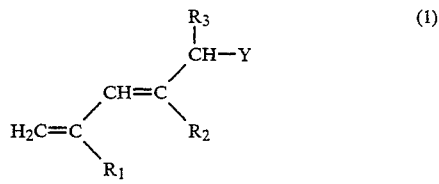

(1)

in which the radicals $R_1$, $R_2$, and $R_3$, which may be identical or different, are each a hydrogen atom, a $C_1$–$C_6$ linear or branched alkyl radical, a phenyl radical, an alkoxycarbonyl radical, an alkoxy radical, and an acylamino radical, wherein the alkyl moiety is a $C_1$–$C_6$ linear, cyclic, or branched alkyl radical, a phenoxycarbonyl radical, or a cyano radical; and the radical Y is a radical X—$R_4$ or —CH($R_5$, $R_6$), wherein $R_4$ is a $C_1$–$C_6$ linear or branched alkyl radical, a phenyl radical, or an acyl radical which comprises a $C_1$–$C_6$ linear or branched alkyl moiety; X is an S or O heteroatom; $R_5$ is an electron-absorbing radical selected from among a cyano, carbamoyl, phenyloxycarbonyl, alkoxycarbonyl, and phenylcarbonyl radical, the linear, cyclical, or branched alkyl moieties of which having from 1 to 6 carbon atoms ($C_1$–$C_6$); and $R_6$ is an electron-donor radical selected from among an alkylthioether, phenylthioether, amino, alkylamino, alkoxy, and phenoxy radical, the linear, cyclic, or branched alkyl moieties of which having from 1 to 6 carbon atoms.

DETAILED DESCRIPTION OF PREFERRED EMBODIMENTS OF THE INVENTION

More particularly according to the present invention, the preferred conjugated diene chain-transfer agents of formula (1) have the formulae:

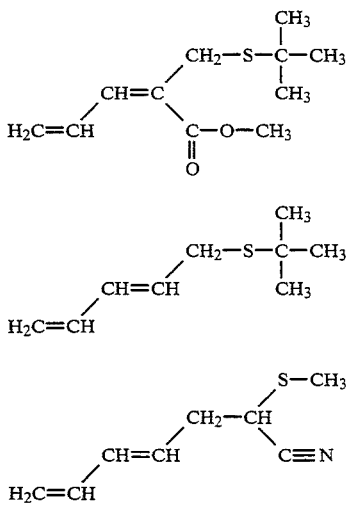

The present invention also features a process for polymer preparation in which at least one ethylenically unsaturated monomer is polymerized, preferably in aqueous emulsion, by radical polymerization in the presence of an effective amount of a transfer agent corresponding to formula (1). Among such ethylenically unsaturated monomers, particularly preferred are styrene, butadiene, (meth)acrylic esters, and vinyl nitriles. By (meth)acrylic esters are intended $C_1$-$C_{12}$ alcohol esters of acrylic acid and methacrylic acid and preferably $C_1$-$C_8$ alcohols, such as methyl acrylate, ethyl acrylate, propyl acrylate, n-butyl acrylate, isobutyl acrylate, 2-ethylhexyl methacrylate, methyl methacrylate, ethyl methacrylate, n-butyl methacrylate, isobutyl methacrylate, etc. The vinyl nitriles include those having 3 to 12 carbon atoms, in particular acrylonitrile and methacrylonitrile. The styrene may be replaced, whether totally or partially, by alpha-methylstyrene or methacrylonitrile.

More specifically, the ethylenically unsaturated monomers to be polymerized comprise at least 60% by weight of at least one of the aforementioned monomers mixed with up to 40% by weight of at least one other ethylenically unsaturated comonomer copolymerizable therewith.

Exemplary ethylenically unsaturated comonomers that are copolymerizable with the aforesaid monomers, in a proportion of up to 40% by weight of the total monomer weight, include:
  (i) vinyl esters of carboxylic acids, such as vinyl acetate, vinyl versatate, and vinyl propionate;
  (ii) ethylenically unsaturated mono- and dicarboxylic acids, such as acrylic acid, methacrylic acid, itaconic acid, maleic acid, fumaric acid, and the monoalkylesters of such carboxylic acids, the alkyl moieties of which preferably having 1 to 4 carbon atoms, and the N-substituted derivatives thereof;
  (iii) amides of unsaturated carboxylic acids, such as acrylamide, methacrylamide, N-methylolacrylamide, and methacrylamide;
  (iv) ethylene monomers bearing a sulfonic acid substitutent and alkali or ammonium salts thereof, e.g, vinylsulfonic acid, vinylbenzene sulfonic acid, α-acrylamidomethylpropane-sulfonic acid, and 2-sulfoethylenemethacrylate;
  (v) ethylenically unsaturated monomers containing a secondary, tertiary, or quaternary amino group or a heterocyclic group containing nitrogen, e.g., vinylpyridines, vinylimidazole, aminoalkyl (meth)acrylates, and aminoalkyl (meth)acrylamides, such as dimethylaminoethylacrylate or dimethylaminoethyl methacrylate, ditertiobutylaminoethylacrylate or -methacrylate, dimethylaminomethylacrylamide or -methacrylamide, as well as zwitterionic monomers, such as sulfopropyl(dimethyl)aminopropyl acrylate, etc.;
  (vi) esters of (meth)acrylic acids with alkanediols prefrably containing 2-8 atoms of carbon, such as ethylene glycol mono(meth)acrylate, hydroxypropyl mono(meth)acrylate, 1,4-butanediol mono(meth)acrylate, as well as monomers containing polymerizable double bonds, such as ethylene glycol dimethacrylate.

The polymerization is conventionally carried out, in solution, in mass, or in aqueous emulsion, in the presence of at least one radical catalyst and of the transfer agent and having a monomer concentration in the reaction medium typically ranging from 20% to 60% by weight.

Any type of catalyst or initiator incorporating the typical free radicals in radical polymerization may be used. Exemplary catalysts include the hydroperoxides, e.g., hydrogen peroxide, diisopropylbenzene hydroperoxide, sodium, potassium, or ammonium persulfates, and cationic catalysts such as azobis (isobutyronitrile) and 4,4'-azobis(4-cyanovaleric acid).

These catalysts may be combined with a reducing agent, e.g., bisulfite. The amount of catalyst typically ranges from 0.05% to 2% by weight in relation to the proportion of monomers.

The amount of diene corresponding to formula 1 generally ranges from 0.05% to 10%, and preferably from 0.1% to 3% by weight in relation to the total weight of the monomers, depending on the molecular weight and the degree of crosslinking desired for the polymer. The diene may be added to the reaction medium either in its entirety at the beginning of the reaction, continuously in solution in the principal monomers, or partially at the beginning and partially continuously. When the solubility of the product in the monomers is low, it may be added as a suspension simultaneously with the monomers.

The polymerization temperature, which depends on the catalyst used, generally ranges from 50° C. to 100° C., and preferably from 70° to 90° C. When polymerization is carried out in an aqueous emulsion, particle stabilization is ensured, if necessary, by any colloidal stabilization system, e.g., anionic, cationic, amphoteric, and non-ionic emulsifiers. Polymerization may be carried out continuously, discontinuously, or semi-continuously, by adding a portion continuously; or it may of the "seeded" or "incremental" type in accordance with any known embodiment designed to produce particles of polymer having a homogeneous and heterogeneous structure.

The odorless polymers and copolymers prepared according to the process of the invention are characterized in that they contain, at the ends of the (co)polymer chains, conjugated dienes emanating from the subject transfer agents. These conjugated diene endgroups provide desirable functionality, for example for copolymerization or subsequent crosslinking, or for the synthesis of block copolymers.

The solutions in an organic solvent, or the aqueous dispersions of polymers, may advantageously be used as binding agents in paper coating compositions and in the textile industry, in particular for the manufacture of non-woven substrates, and as additives in paints and adhesive formulations.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Preparation of the transfer agent having the formula

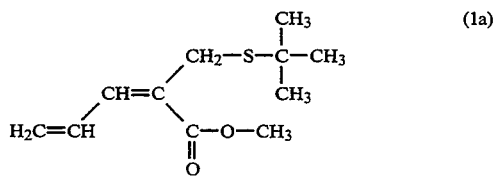

The compound corresponding to formula 1a was prepared by reacting tertiobutylthiol with the methyl ester of 2-methyl-4-(bromomethyl)-1,3-pentanediehoic acid, itself prepared via bromination, with PBr₃, of 2-methyl-3-hydroxy-4-methoxycarbonyl-1,4-butadiene, in turn produced by condensation of methyl acrylate with methacrolein.

A mixture of 13 grams (0.15 mole) methyl acrylate, 7 grams (0.1 mole) methacrolein, and 1.6 grams (0.015 mole) DABCO (diazabicyclooctane) was stirred at ambient temperature for 21 days. The unreacted starting materials were removed by means of rotavapor. The residue was dissolved in 50 ml ether and washed with 100 ml of a 10% hydrochloric acid solution (aqueous), then twice with 100 ml water. After evaporation of the ether, 10.1 grams (yield: 65%) of liquid (2-methyl-3-hydroxy-4-methoxycarbonyl-1,4-butadiene) were obtained A solution of PBr₃ (10 grms, 0,037 mole) in ether was added to a solution of 2-methyl-3-hydroxy-4-methoxycarbonyl-1,4-butadiene (7.7 grams, 0.05 mole) in ether (100 ml), maintained at −10° C. The reaction was exothermic and released HBr. The solution was stirred and maintained at ambient temperature for three hours. The temperature was decreased to −10° C. and 100 ml deionized water were added. The mixture was extracted using hexane (3×20 ml), and the organic phase was washed twice with a saturated aqueous solution of sodium chloride and dried on MgSO₄. The solvent was evaporated and a liquid (methyl ester of 2-methyl-4-(bromomethyl)-1,3-pentadienoic acid) was obtained (10.5 grams; yield: 96%).

1.37 grams of potassium carbonate (0.01 mole), 2.19 grams of the methyl ester of 2-methyl-4-(bromomethyl)-1,3-pentadienoic acid (0.01 mole), 0.9 gram t-butylthiol (0.01), and 50 ml of methanol were stirred for 20 hours. The methanol was evaporated using a rotavapor and 20 ml of water were added. The aqueous phase was washed three times in 20 ml ether, and the organic phases were combined and dried on MgSO₄. The solvent was evaporated and the product was distilled under reduced pressure. 2 grams of the compound corresponding to formula (1a) were obtained (yield by weight: 87%).

EXAMPLE 2

Preparation of polystyrene in the presence of the transfer agent having formula (1a)

70 mg azobisisobutyronitrile (AIBN) were added to 45 grams newly-distilled styrene, and 4.5 grams of the mixture were placed in a 100 ml flask containing the amount, indicated in Table 1 below, of the compound corresponding to formula (1a). The mixture was polymerized for one hour at 60° in the absence of oxygen, then precipitated using an excess quantity of methanol. The polymer was then collected and dried until it reached constant weight. The polymer was then analyzed using gel-permeation chromatography (GPC), tetrahydrofuran being used as eluent, at a delivery rate of 1 ml/mn. The apparatus included a WATERS ® pump connected to 4 PLGEL ® columns (pore size: 10⁵ and 50 nm) and two mixed columns whose pore sizes ranged from 50 to 10⁻³ nm and a differential refractometer. The system was calibrated using standard measure polystyrene of known molecular weight and low polydispersity.

The results obtained are reported in Table 1 below:

TABLE 1

| Quantity of transfer agent (1a) (mg) | Conversion (%) | Mn* (× 1,000) |
|---|---|---|
| 0 | 2.6 | 103 |
| 49 | 0.55 | 11 |

Mn*: number average molecular weight in grams/mol.

The results summarized in Table 1 indicate that the compound of formula (1a) was a very effective transfer agent.

EXAMPLE 3

Preparation of poly(methyl methacrylate) in the presence of the transfer agent having formula (1a)

The procedure was identical to that of Example 2, except that the styrene was replaced by methyl methacrylate and that quantities of transfer agent indicated in Table 2 below were used:

TABLE 2

| Quantity of transfer agent (1a) (mg) | Conversion (%) | Mn* (× 1,000) |
|---|---|---|
| 0 | 2.8 | 201 |
| 13 | 0.7 | 48 |

Mn*: number average molecular weight in polystyrene equivalents in g/mol.

The results reported in Table 2 indicate that the compound of formula (1a) was a very effective transfer agent.

EXAMPLE 4

Preparation of the transfer agent having the formula

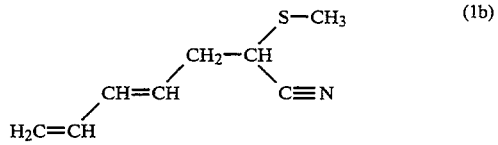

The compound corresponding to formula (1b) was prepared via bromination of 1,4-pentadiene-3-ol, followed by reacting methylthioacetonitrile with the 5-bromo-1,3-pentadiene thus prepared.

A solution of PBr₃ (10 grams; 0,037 mole) in ether was added to a solution of 1,4-pentadiene-3-ol (4.2 grams; 0.05 mole) in ether (100 ml), maintained at −10° C. The reaction was exothermic and released HBr. The solution was stirred and maintained at ambient temperature for three hours. The temperature was once again decreased to −10° C., and 10 ml of water were added. The mixture was extracted using hexane (3×20 ml), and the organic phase was washed twice with a saturated aqueous solution of NaCl and dried on MgSO₄. The solvent was evaporated, and 5-bromo-1,3-pentadiene was obtained (7 grams; weighted yield: 95%).

A solution of 0.6 g (0.02 mole) of NaH in dry THF insulated from air and water and 1.8 g (0.02 mole) of methylthioacetonitrile were added dropwise. The solution was stirred at ambient temperature for 15 minutes, and 3 g (0.02 mole) of 5-bromo-1,3-pentadiene were added at ambient temperature. 100 ml of deionized water were dripped therein and the solution was extracted using ether (3×20 ml), then dried on MgSO₄. The solvent was evaporated and the compound corresponding to formula (1b) was obtained (1.5 g; yield: 50%).

EXAMPLE 5

Preparation of polystyrene in the presence of the transfer agent having formula (1b)

The procedure was identical to that of Example 2, using the amounts of the compound of formula (1b) indicated in Table 3 below, which also reports the results obtained:

TABLE 3

| Quantity of transfer agent (1b) (mg) | Conversion (%) | Mn* (× 1,000) |
|---|---|---|
| 0 | 2.6 | 103 |
| 32 | 0.17 | 10 |

EXAMPLE 6

Preparation of poly(methyl methacrylate) in the presence of the transfer agent having formula (1b)

The procedure was identical to that of Example 3, using the amounts of the compound of formula (1b) indicated in Table 4, which also reports the results obtained:

TABLE 4

| Quantity of transfer agent (1b) (mg) | Conversion (%) | Mn* (× 1,000) |
|---|---|---|
| 0 | 2.8 | 201 |
| 100.2 | 0.02 | 27 |

EXAMPLE 7

Preparation of the transfer agent having formula (1c)

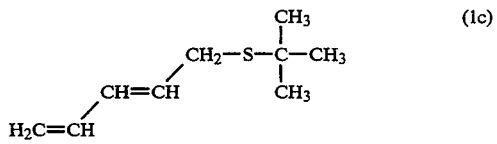

1.37 grams of potassium carbonate (0.01) mole, 1.5 grams of 5-bromo-1,3-pentadiene (0.01 mole), 0.9 grams of t-butylthiol (0.01 mole), and 50 ml of methanol were stirred for 20 hours. The methanol was evaporated using a rotavapor, and 20 ml of water were added. The aqueous phase was washed using 3×30 ml of ether, and the organic phases were combined and dried on $MgSO_4$. The solvent was evaporated and the product distilled under reduced pressure. 1.32 grams of the compound corresponding to formula (1c) were obtained (87% yield by weight).

EXAMPLE 8

Preparation of polystyrene in the presence of the transfer agent having formula (1c)

The procedure was identical to that of Example 2, employing the amounts of compound (1c) indicated in Table 5, which also reports the results obtained:

TABLE 5

| Quantity of transfer agent (1c) (mg) | Conversion (%) | Mn* (× 1,000) |
|---|---|---|
| 0 | 2.6 | 103 |
| 29.8 | 2.02 | 29 |

EXAMPLE 9

Preparation of poly(methyl methacrylate) in the presence of the transfer agent having formula (1c)

The procedure was identical to that of Example 3, employing the amounts of compound (1c) indicated in Table 6, which also reports the results obtained:

TABLE 6

| Quantity of transfer agent (1c) (mg) | Conversion (%) | Mn* (× 1,000) |
|---|---|---|
| 0 | 2.6 | 103 |
| 34.7 | 0.3 | 20 |

EXAMPLE 10

Preparation of polystyrene in the presence of transfer agent (1c)

Styrene, AIBN, and the compound of formula (1c) prepared via the procedure of Example 7 above were mixed in a glass tube in the amounts indicated in Table below. The reaction medium was deaereted by means of three freezing cycles and placed under a vacuum; the tube was then sealed in a vacuum and heated to the indicated temperature. The contents were then diluted in 150 ml of THF and the polymer precipitated out in 1.5 liters of methanol.

After filtration, the polymer obtained was dissolved once again in 15 ml of THF and precipitated out again in 1.5 liters methanol. The filtrate obtained was vacuum-dried at 50° C. until it exhibited constant weight. The polymer was then analyzed using GPC, in accordance with the conditions indicated in Example 2 above.

The results obtained are reported in Table 7 below:

TABLE 7

| | STYRENE | |
|---|---|---|
| Polymerization Conditions | [TAC] *10² mol/l | Mn (× 1,000) g/mol |
| Temp.: 50° C. | 0 | 260.0 |
| [AIBN] 5.92 · 10⁻³ mol/l | 1.32 | 118.0 |
| [Styrene] 8.45 mol/l | 2.50 | 72.9 |
| | 4.28 | 52.5 |
| | 5.78 | 42.3 |
| | 7.47 | 30.4 |
| | 9.27 | 24.1 |
| | 10.59 | 25.0 |
| | 13.78 | 18.1 |
| | 16.58 | 15.3 |
| Temp.: 60° C. | 0 | 163.4 |
| [AIBN] 5.86 · 10⁻³ mol/l | 1.34 | 93.0 |
| [Styrene] 8.37 mol/l | 2.78 | 51.6 |
| | 4.16 | 38.1 |
| | 5.49 | 30.4 |
| | 7.58 | 22.6 |
| | 9.74 | 19.6 |
| | 12.85 | 15.9 |
| | 14.79 | 14.8 |
| | 17.12 | 14.0 |
| Temp.: 70° C. | 0 | 120.2 |
| [AIBN] 2.90 · 10⁻³ mol/l | 1.32 | 69.6 |
| [Styrene] 8.28 mol/l | 2.68 | 45.6 |
| | 3.92 | 35.0 |
| | 5.31 | 27.4 |
| | 6.99 | 22.0 |
| | 8.62 | 20.0 |
| | 10.92 | 16.6 |
| | 13.53 | 14.1 |
| | 16.28 | 12.2 |
| Temp.: 80° C. | 0 | 83.7 |
| [AIBN] 2.87 · 10⁻³ mol/l | 1.97 | 42.5 |
| [Styrene] 8.20 mol/l | 3.65 | 26.8 |
| | 5.20 | 21.8 |
| | 6.15 | 19.7 |

TABLE 7-continued

| | STYRENE | |
|---|---|---|
| Polymerization Conditions | [TAC] *$10^2$ mol/l | Mn (× 1,000) g/mol |
| | 8.19 | 16.0 |
| | 9.78 | 14.6 |
| | 12.97 | 11.8 |
| | 14.74 | 11.1 |
| | 17.67 | 9.5 |

*[TAC]: transfer agent concentration
[AIBN]: AIBN concentration
[Styrene]: styrene concentration

EXAMPLE 11

Preparation of poly(methyl methacrylate) in the presence of compound (1c)

The methyl methacrylate (MMA), AIBN, and the compound of formula (1c) prepared in accordance with Example 7 were mixed in a glass tube in the amounts indicated in Table 8 below. The reaction medium was deaerated using freezing cycles and placed in a vacuum; the tube was then vacuum-sealed and heated to the indicated temperature. The contents were then diluted in 150 ml of THF and the polymer was precipitated out in 1.5 liters of heptane.

The precipitated product was filtered and vacuum-dried at 50° C. until reaching constant weight.

The polymer was then analyzed using GPC under the conditions set forth in Example 2.

The results obtained are reported in Table 8 below:

TABLE 8

| | MMA | |
|---|---|---|
| Polymerization Conditions | [TAC] *$10^2$ mol/l | Mn (× 1,000) g/mol |
| Temp.: 50° C. | 0 | 813.0 |
| [AIBN] 5.88 ·]$10^{-3}$ mol/l | 1.31 | 47.7 |
| [MMA] 9.01 mol/l | 2.22 | 28.2 |
| | 3.45 | 23.7 |
| | 5.15 | 18.8 |
| | 7.76 | 9.6 |
| | 9.62 | 8.3 |
| | 11.2 | 7.4 |
| Temp.: 60° C. | 0 | 610.0 |
| [AIBN] 5.80 · $10^{-3}$ mol/l | 0.61 | 70.1 |
| [MMA] 8.91 mol/l | 1.21 | 43.3 |
| | 1.83 | 32.2 |
| | 3.05 | 24.3 |
| | 4.27 | 19.6 |
| | 6.52 | 12.5 |
| | 7.70 | 10.0 |
| | 9.10 | 8.8 |
| Temp.: 70° C. | 0 | 515.0 |
| [AIBN] 5.72 · $10^{-3}$ mol/l | 0.59 | 58.2 |
| [MMA] 8.78 mol/l | 1.19 | 35.8 |
| | 1.80 | 29.1 |
| | 3.00 | 23.4 |
| | 4.21 | 18.4 |
| | 7.78 | 8.3 |
| | 8.95 | 7.9 |
| | 10.6 | 6.8 |
| Temp.: 80° C. | 0 | 272.0 |
| [AIBN] 2.82 · $10^{-3}$ mol/l | 1.14 | 35.8 |
| [MMA] 8.66 mol/l | 2.00 | 25.5 |
| | 3.17 | 20.3 |
| | 4.86 | 10.9 |
| | 6.22 | 94.7 |
| | 7.41 | 88.0 |
| | 9.43 | 71.1 |
| | 10.7 | 62.1 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an addition (co)polymer, comprising polymerizing at least one olefinically unsaturated monomer in the presence of an effective amount of a conjugated diene chain-transfer agent having the formula (1):

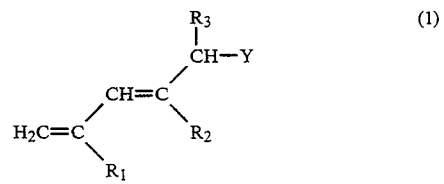

in which $R_1$, $R_2$ and $R_3$, which may be identical or different, are each a hydrogen atom, a $C_1$-$C_6$ linear or branched alkyl radical, a phenyl radical, an alkoxycarbonyl, alkoxy or acylamino radical, the alkyl moieties of which being $C_1$-$C_6$ linear, branched or cyclic alkyl radicals, a phenoxycarbonyl radical, or a cyano radical; Y is a radical X-$R_4$ or —CH($R_5$, $R_6$), wherein $R_4$ is a $C_1$-$C_6$ linear or branched alkyl radical, a phenyl radical, or a $C_1$-$C_6$ linear or branched acyl radical; X is 0 or S; $R_5$ is an electron-attracting radical; and $R_6$ is an electron-donating radical.

2. The process as defined by claim 1, wherein said conjugated diene of formula (1), $R_5$ is a cyano radical, a carbamoyl radical, a phenyloxycarbonyl radical, an alkoxycarbonyl radical, the alkyl moiety of which being a $C_1$-$C_6$ linear, branched or cyclic alkyl radical, or a phenylcarbonyl radical; and $R_6$ is a phenylthioether radical, and amino radical, a phenoxy radical, or an alkylthioether, alkylamino or alkoxy radical, the alkyl moieties of which being $C_1$-$C_6$ linear, branched or cyclic alkyl radicals.

3. The process as defined by claim 1, said at least one olefinically unsaturated monomer comprising styrene, butadiene, a (meth)acrylic ester, or a vinyl nitrile.

4. The process as defined by claim 3, said at least one olefinically unsaturated monomer further comprising up to 40% by weight of at least one comonomer selected from among a vinyl carboxylic acid ester, an ethylenically unsaturated mono- or dicarboxylic acid, an ethylenically unsaturated carboxylic acid amide, an ethylenically unsaturated sulfonic acid, or an alkanediol ester of a (meth)acrylic acid.

5. The process as defined by claim 1, carried out in the presence of from 0.05% to 10% by weight of said conjugated diene of formula (1), based on the total weight of said at least one olefinically unsaturated monomer.

6. The process as defined by claim 5, carried out in the presence of from 0.1% to 3% by weight of said conjugated diene of formula (1).

7. The process as defined by claim 1, comprising a bulk polymerization.

8. The process as defined by claim 1, comprising a solution polymerization in an organic solvent.

9. The process as defined by claim 1, comprising an aqueous emulsion polymerization.

10. The process as defined by claim 1, carried out in the presence of a radical polymerization initiator.

11. The (co)polymer product of the process as defined by claim 1.

* * * * *